(12) United States Patent
Cheeseright et al.

(10) Patent No.: US 7,805,257 B2
(45) Date of Patent: Sep. 28, 2010

(54) COMPARISON OF MOLECULES USING FIELD POINTS

(75) Inventors: Tim Cheeseright, Hertfordshire (GB); Mark Denis Mackey, Hertfordshire (GB); Jeremy Gilbert Vinter, Hertfordshire (GB)

(73) Assignee: Cresset Biomolecular Discovery Limited, Hertfordshire (GB)

( * ) Notice: Subject to any disclaimer, the term of this patent is extended or adjusted under 35 U.S.C. 154(b) by 236 days.

(21) Appl. No.: 10/526,335

(22) PCT Filed: Aug. 18, 2003

(86) PCT No.: PCT/GB03/03605

§ 371 (c)(1),
(2), (4) Date: Nov. 16, 2005

(87) PCT Pub. No.: WO2004/023349

PCT Pub. Date: Mar. 18, 2004

(65) Prior Publication Data

US 2006/0129323 A1    Jun. 15, 2006

(30) Foreign Application Priority Data

Sep. 6, 2002   (GB) .................................. 0220785.0

(51) Int. Cl.
*G01N 31/00*   (2006.01)
(52) U.S. Cl. .......................................... 702/30; 703/12
(58) Field of Classification Search ...................... None
See application file for complete search history.

(56) References Cited

U.S. PATENT DOCUMENTS 5,703,792 A   12/1997   Chapman

FOREIGN PATENT DOCUMENTS

| GB | 2 266 391 | 10/1993 |
| GB | 2 317 030 | 3/1998 |
| WO | 92/22875 | 12/1992 |
| WO | 98/47088 | 10/1998 |

OTHER PUBLICATIONS

Mestres et al. (Journal of Computer-Aided Molecular Design, vol. 13, pp. 79-93, 1999).*
Mestres et al (J. Molecular Graphics and Modeling, vol. 15, p. 114-121, 1997).*
Maggoria et al. (Journal of Mathematical Chemistry vol. 31, No. 3, Apr. 2002).*
Vinter, J.G. et al. "Multiconformational composite molecular potential fields in the analysis of drug action. I. Methodology and first evaluation using 5-HT and histamine action as examples." *Journal of Computer-Aided Molecular Design.* 9.4 (Aug. 1995): 297-307.
Apaya, Robert P. et al. "The matching of electrostatic extrema: A useful method in drug design? A study of phosphodiesterase III inhibitors." *Journal of Computer-Aided Molecular Design.* 9.1 (Feb. 1995): 33-43.
Vinter, J.G., "Extended electron Distribution applied to the molecular mechanics of some intermolecular interactions." Journal of Computer-Aided Molecular Design, 8 (1994) 653-668.

* cited by examiner

*Primary Examiner*—Karlheinz R Skowronek
(74) *Attorney, Agent, or Firm*—Renner, Otto, Boisselle & Sklar, LLP

(57) ABSTRACT

A method of comparing two conformers in which an overlay score is obtained, comprises providing a set of field points representing field extrema of a first molecule, wherein each field point has a position and a field size value; determining at the position of each of the field points of the first molecule the field of a second molecule to obtain a set of field sample values; and combining the field sample values with the field size values to obtain a score indicative of the field similarity of the first molecule to the second molecule. The method overcomes a limitation of conventional pseudo-Coulombic scoring in which a low score is achieved when extrema of large extent overlap but have their minimum points widely separated. The method can be applied to molecular mechanics modeling using atom centered charges (ACCs) and extended electron distributions (XEDs) as well as to quantum mechanics models.

14 Claims, 1 Drawing Sheet

COMPARISON OF MOLECULES USING FIELD POINTS

This application is a national phase of International Application No. PCT/GB2003/003605 filed Aug. 18, 2003 and published in the English language.

BACKGROUND OF THE INVENTION

The invention relates to molecular modelling for drug discovery, more especially to molecular modelling using field point representations of the molecular field.

In pharmaceutical research, the aim is often to find a small molecule which interacts with a larger molecule, referred to as a target, in a specific manner. In most cases this larger molecule is a protein. Often, the process of drug discovery is an attempt to find a small organic molecule which will bind strongly to a specific region of a specific protein, and which also possesses good pharmacokinetic qualities.

The drug discovery process has traditionally been a fairly hit-and-miss affair. Initially a compound is found that binds to the target, this initial compound of interest being referred to as a lead compound, or lead for short. Leads are usually either natural products or are identified by screening large sets of compounds against the target in the hope of a chance match. Once one or more leads have been identified, a process of optimisation is carried out by medicinal chemists who make incremental changes to the lead molecule in the hope of improving its pharmaceutical properties.

In recent years theoretical chemistry and molecular modelling have become increasingly important in both lead finding and lead optimisation. Modellers attempt to generate new leads by examination of the common features of existing active compounds and by examination of the structure of the target protein if it is known. They also assist in the process of lead optimisation by predicting which changes to the lead structure are likely to be beneficial.

A molecule's affinity to a target of known or unknown structure can be estimated by reference to its similarity to other compounds, both active and inactive. To do this, the modeller is required to calculate intermolecular interactions.

It is possible to predict the binding properties of an untested molecule by representing the physical properties of a molecule which are important in its binding to other molecules, and then assessing the similarity between two such sets of physical properties, one for the untested molecule and one for a well characterised molecule.

Accurate molecular modelling is possible using advanced quantum mechanics. However, the computational effort needed for quantum mechanics is prohibitive for most biologically relevant molecules.

An alternative approach is called molecular mechanics. Molecular mechanics represents the molecule in a simple Newtonian fashion as a collection of balls and springs. The principles of molecular mechanics are simple and empirical. Moreover, molecular mechanics is computationally fast enough to cope with large proteins and other biopolymers associated with drug design.

In traditional molecular mechanics the electrostatic properties of a molecule are defined by placing a point charge at the centre of each atom (atom-centred charges or ACCs). Many different methods for calculating or estimating the value of such point charges are described in the literature. The aim of ACC methods is to distribute the point charges in such a way that the resulting electrostatic field is as similar as possible to the true electrostatic field (as determined by quantum mechanics methods). The electrostatic field as approximated by ACCs is usually quite accurate at a distance from the molecule (>5 Å), but can be quite inaccurate at the molecular surface.

To improve the quality of molecular mechanics models at the molecular surface, extended electron distributions (XEDs) have been developed. The XED method involves replacing the point charge at the centre of some atoms with a set of point charges, one at the centre of the atom and one or more others distributed around that atom a short distance away. The XED method is described in Vinter (1994) [1] and Vinter and Trollope (1995) [2]. In the XED method, the XEDs themselves are treated simply as extra atoms which have charge but no volume. XED methods can therefore calculate electrostatic interactions more accurately than ACC methods, while retaining the speed advantages of the molecular mechanics framework.

Quantum mechanical models and molecular mechanical models, such as ACC or XED models, can use the concept of field points to represent the molecular field. In this approach, the conformation of a molecule, i.e. its equilibrium arrangement either in isolation or when bound to another specific molecule or surface, is represented by a set of field points which measure field strength at a relatively small number of field maxima and minima around the molecule which are relevant to how the molecule is likely to interact with other molecules.

In order to calculate field points, a field definition must be adopted. One known field definition for molecular mechanical models uses positive and negative electrostatic interaction fields in combination with a surface interaction field. The two electrostatic interaction fields are defined by the interaction energy of a specific charged 'probe' molecule with the molecule of interest. For example, a probe the size of an oxygen atom, with either a +1 or a −1 elemental charge, can be used. The field value at a given point is the interaction energy of the molecule with the probe atom sited with its centre at that point. The surface interaction field is defined by the van der Waals interaction energy of a neutral 'probe' with the molecule, for example an uncharged oxygen atom.

Other field definitions have been used, for example ones that include electrostatic fields calculated from quantum molecular methods, and ones that include hydrophobic fields calculated from the electrostatic field and its partial derivatives. In principle, any field definition can be used provided that its value can be defined at any point in space around the molecule.

Once the field definition has been made, the field points of the molecule need to be calculated. With the molecular modelling approach, the field points are subdivided into a number of subsets, one for each field type, with each subset being calculated separately. The field points for a molecule are the values and locations of the extrema of its field, i.e. maxima and minima. The final set of field points from each field type can be filtered to remove duplicate extrema and small extrema if desired.

The field point set encodes a large amount of information about the properties of the molecule, especially regarding its interaction with other molecules. The electrostatic field points encode information about the preferred hydrogen-bonding environment of the molecule, while the surface interaction field points encode the molecule's steric bulk.

The basic assumption underlying the field point approach is that two molecules which have similar sets of field points should have similar interactions with other molecules and hence should have similar biological activities. In other words, if molecule A has a certain biological activity, and molecule B is calculated to be similar to molecule A in a relevant conformation, then it is concluded that molecule B potentially has the same biological activity.

With the field point approach, the similarity between conformations of two molecules is calculated according to a scoring formula which is sensitive to differences between the field point positions and energy values of the field points in the two field point sets. The result of the formula, i.e. the score, is a scalar quantity referred to as the field similarity value. The act of comparing fields from two molecules is sometimes referred to as field overlay or a field overlay process by virtue of the fact that the calculation of the field overlay score requires an alignment of the two molecules.

By way of example, suppose that molecules A and B are to be compared for similarity. Molecule A is known to bind to a particular protein. The conformation of A when bound to that protein is also known. Molecular B is a new candidate molecule for potentially binding to the same protein. To carry out the comparison calculation, the bound conformation of A is compared to multiple conformations of B. Multiple conformations of B are tried, since, if B is able to bind to the protein, the conformation of B which allows such binding is not yet known.

In another example, the bound conformation of molecule A may not be known, even though it is known that molecule A binds to a particular protein. In that case, the comparison process will compare multiple conformations of A successively with multiple conformations of B.

The comparison process comprises two stages. The first stage is an alignment step of determining an alignment between the conformers of A and B. The second stage is a scoring step of calculating the field similarity for the aligned position.

In practice, the two stages are often carried out iteratively. After an initial approximate alignment, fine alignment may be an automated process of maximising the score, i.e. the field similarity value, through incremental changes in the alignment. It is noted that the initial alignment may be a completely random one (in a Monte-Carlo type process). The comparison process can be carried out independently for each field type in a molecular mechanics model. A field similarity value is calculated independently for each field, referred to as a field similarity subvalue in the following, and a weighted sum is taken to be the overall field similarity value.

The scoring step, i.e. the field similarity calculation, is critically important, since the field similarity value is the ultimate measure of the potential of candidate molecule B to have the same biological activity as molecule A.

In the XED model of Vinter and Trollope (1995) [2], the method used to calculate the field similarity value for a given alignment of two conformers A and B is now described. It is recalled that Vinter and Trollope use a field definition having three field types, namely positive and negative electrostatic fields and a surface interaction field.

A pseudo-Coulombic potential is defined between the field points on molecule A and the field points on molecule B and the value of this potential function is calculated. The pseudo-Coulombic potential treats each field point as if it were a point charge in space with its charge being the energy value of the field point. A pseudo-potential energy is then calculated between these sets of point pseudo-charges. The +ve electrostatic field and −ve electrostatic field points are allowed to interact (being assigned positive and negative charges respectively), but the pseudo-Coulombic potential is calculated separately for the surface interaction field points. The higher the potential calculated with this method, the more similar the two conformers are taken to be.

In the XED model of Vinter and Trollope (1995) [2], although not directly described in the paper, each of the field similarity subvalues was determined according to the following pseudo-Coulombic potential formula:

$$E_{AB} = -\sum_{i,j} \frac{q_{iA} q_{jB}}{k + d_{iA,jB}^l}$$

where $q_{iA}$ is the energy value of the ith field point on molecule A (labelled q in view of the Coulomb analogy being used), $q_{jB}$ is the energy value of the jth field point on molecule B, $d_{iA,jB}$ is the distance between the ith field point on molecule A and the jth field point on molecule B, the sum is over all field points i on molecule A and j on molecule B, k is a constant with a value of 1, and l is a constant with a value of 1. The constant k was added into the usual Coulomb formula to avoid the pseudo-Coulombic energy value becoming too large for field point pairs that are very close (i.e. when distance d is very small) and thereby distorting the results.

Other prior art is described in references [3]-[6].

SUMMARY OF THE INVENTION

According to a first aspect of the invention there is provided a method of comparing molecules, comprising: providing a set of field points representing field extrema of a first molecule, wherein each field point has a position and a field size value; determining at the position of each of the field points of the first molecule the field of a second molecule to obtain a set of field sample values; and combining the field sample values with the field size values to obtain a score indicative of the field similarity of the first molecule to the second molecule.

The term field sample value is used to refer to the field from the second molecule at the first molecule's field point. This term is chosen since the method effectively samples the second molecule field at positions determined by the positions of the field points of the first molecule. The field sample values are thus field points of the second molecule, but not at field extrema positions of the second molecule. Thus, although the field sample values form a set of field points, this is not in the conventional sense of a field point representation of a molecule's extrema.

The field extrema may be minima only, maxima only or minima and maxima. In most cases, the field can be defined such that the areas of interest have a negative value, and hence the extrema of interest are confined to field minima only. The field size values may be energy values or any other suitable scalar field parameter. For example, the scalar force values can be useful in some circumstances.

The invention is based on the recognition that, in the overlay process, the aim is to find the overlay that maximises the similarity of the overall fields of molecules A and B. Ideally, for a given orientation one would integrate the product of molecule A's and molecule B's fields over all space but that would take far too long. The strength of the field point representation is therefore also a weakness when carrying out the overlay process, in that the molecular field has been collapsed down to a collection of field points indicating significant field minima and maxima, but nothing else. Specifically no information is retained about the spatial extent of any of the field extrema catalogued by the set of field points.

A common occurrence, especially for the electrostatic fields, is for there to be a very broad region of space around a molecule A where the field has a high value, but for that region to only have one minimum point, and hence only one field point representing it. If another molecule B also has a field point associated with a field minimum of large spatial extent, then placing this field point anywhere around molecule A where molecule A's field has a high value is in reality a good overlay. However, with the pseudo-Coulombic method used in the model of Vinter and Trollope (1995) [2] this situation will not necessarily give a good overlay score. A poor overlay score will result if there is a large distance between molecule A's field point and molecule B's field point, even though the overlap integral of the two fields in this region has a high value.

The invention overcomes this limitation of the pseudo-Coulombic scoring method, by providing a method in which the score is obtained by determining the field value for molecule B at the coordinates of molecule A's field point. Molecule A's field point no longer has to be very close to molecule B's field point to get a good overlay score: it just needs to be in a region where molecule B's field is large. The improvement constituted by the method of the invention in relation to the pseudo-Coulombic scoring method is a consequence of it being a closer approximation to performing an integration over all space of the field overlaps between molecule A's field and molecule B's field.

The field sample values (i.e. the values of second molecule's fields at the first molecule's field point positions) can be determined by applying the position of each of the field points to a field definition formula, typically the field definition formula used to calculate the field points. Alternatively, the field sample values can be determined by calculating the fields by interpolation from a pre-calculated grid of field size values around the second molecule.

The method can further comprise: providing a set of field points representing field extrema of the second molecule, wherein each field point has a position and a field size value; determining at the position of each of the field points of the second set the field of the first molecule to obtain a further set of field sample values; combining the further field sample values with the field size values of the field points of the second set to obtain a further score, wherein the further score is indicative of the field similarity of the second molecule to the first molecule; and combining the further score with the score of the field similarity of the first molecule to the second molecule to obtain an aggregate score. The advantage of this approach is that the aggregate score is independent of the order in which the comparison has been carried out.

A problem with the scoring used in conventional overlay methods is that a molecule with one large field point, e.g. of size 2S, gives a different score from a molecule with two smaller well-separated field points, each of size S. It would be desirable for the overlay score of both molecules on themselves to be roughly the same in both cases, as the sum of the field point sizes of the two molecules is the same.

A further aspect of the invention provides a computer interpretable medium bearing a set of instructions for carrying out the methods of the invention. The computer interpretable medium may be a signal carrier medium, for example an electrical signal carried along a conductive path, an optical signal carried along an optical fibre, or a wireless signal carried in the air, as used to distribute computer readable instruction sets from computer to computer within and between jurisdictions. The computer interpretable medium may also be a recording medium, for example a magnetic or optical storage medium, or a latent or non-latent computer memory device.

Another aspect of the invention provides a computer apparatus configured to carry out the methods of the invention.

The computer apparatus may be configured in hardware, firmware or software, or in a combination thereof.

According to another aspect of the invention there is provided a solution to this problem in the form of a method of comparing molecules, comprising: providing first and second sets of field points representing fields around first and second molecules, wherein each field point has a position and a field size value; and combining the field size values of the first and second sets of field points to obtain a score indicative of the field similarity of the first molecule to the second molecule, wherein the field size values are transformed to scaled field size values prior to applying a scoring formula such that two field points having a first field size value give the same contribution to the score as one field point having a field size value twice the first field size value.

In an embodiment of this other aspect of the invention, the scaled field size values have the magnitude of the square root of the absolute field size values and the sign of the field size values.

The field points of the first and second sets may represent field extrema of the first and second molecules respectively, as in the prior art. Alternatively, the field points of the first set represent field extrema of the first molecule and the field points of the second set represent the field of the second molecule at the positions of the field points of the first molecule, as in the first aspect of the invention.

BRIEF DESCRIPTION OF THE DRAWING

For a better understanding of the invention and to show how the same may be carried into effect reference is now made by way of example to the accompanying drawing in which.

DETAILED DESCRIPTION

Figure 1:
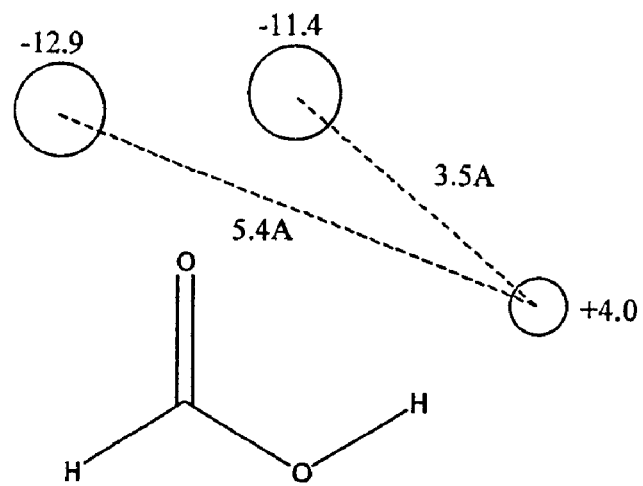
FIG. 1 shows formic acid and a field point representation thereof.

Application of the invention to a molecular mechanics model is now described by way of example.

For each field point on a first molecule A, the value of the appropriate field at the corresponding point on a second molecule B is calculated. This is done by applying a field definition formula for the field type concerned. The field definition formulae used will be those used to calculate the field points. Example field definitions are given in Vinter and Trollope (1995) [2], in particular by equations 1-6 of this paper. The product of molecule A's field point value and the value of molecule B's field at that point is taken as the interaction energy for that field point, and the sum of these interaction energies over all of molecule A's field points gives the similarity of molecule B to molecule A. The scoring formula can be expressed as:

$$E_{AB} = -\sum_i q_{iA} f_B(\underline{p}_{iA})$$

where $q_{iA}$ is the energy value of the ith field point on molecule A, $f_B(\underline{p}_{iA})$ is the value of molecule B's field at the position $\underline{p}_{iA}$ of the ith field point on molecule A, and the sum is over all field points i on molecule A.

Since this procedure is not symmetrical, a separate score may be determined for the similarity of molecule A to molecule B, i.e.

$$E_{BA} = -\sum_j q_{jB} f_A(p_{jB})$$

where $q_{jB}$ is the energy value of the jth field point on molecule B, $f_B(p_{jB})$ is the value of molecule A's field at the position $p_{jB}$ of the jth field point on molecule B, and the sum is over all field points j on molecule B.

It is noted that the negative signs are included here since we follow the convention that the more negative $E_{AB}$, the better the overlay. This convention is also followed above in the description of the prior art method. (Alternatively, all the negative signs could be removed in which case a more positive the value of $E_{AB}$ the better the overlay.) These two scores may be averaged or otherwise combined to give an aggregate score, thereby providing a single value of the score for the similarity between molecule A and molecule B, i.e.

$$E = (E_{AB} + E_{BA})/2$$

As an alternative, rather than calculating the exact value of the field at the point on molecule B corresponding to each field point on molecule A, the field value on molecule B can be estimated by interpolation from a pre-calculated grid of field values around B. This method is generally faster, but this speed increase is at the expense of accuracy.

The values of the field points may be scaled before the field similarity calculation. One enhancement which has been found to improve the usefulness of the overlay energies (i.e. the scores) is to scale down field points on a molecule which are very close to other field points of the same field type on the same molecule. This prevents a conformer with a cluster of many large field points from dominating the overlays.

One scale method which is used in the present implementation of the system is now described. For a given field point A in a molecule, we calculate $$D = \sum_B \left( \frac{q_B}{q_A} \cdot \frac{1}{1 + \left(\frac{d}{\alpha}\right)^2} \right)$$

where the sum is over all field points B on the same molecule of the same type, $q_A$ and $q_B$ are the energies of each pair of field points, d is the distance between each pair of field points, and $\alpha$ is a scaling parameter (we use 2.0). Molecule A's field point energy is then divided by (1+D). This scaling factor has the property that if two field points coincide, each will be halved in size, and as they move further apart their sizes increase gradually back to their 'normal' size.

The alignment of the two conformers may be performed manually or by one of a number of automatic methods. The simplest of these simply involves starting from a random orientation of A and B and using an optimising technique (such as a simplex) to move B around until the interaction score is maximised. This procedure is repeated a number of times and the best (i.e. highest-scoring) overlay is kept.

Alternatively, an alignment can be generated algorithmically based on the field point patterns (by matching pairs of field points with a clique-detection algorithm, for example) and this can then optionally be optimised. In either case, the optimisation process can involve first using a coarse rapid method of assessing field similarity and then using a more refined method which requires a greater amount of computation.

In particular, the alignment may first be optimised using the alternative method described above based on interpolation from a pre-calculated grid, or by the method previously used in the model of Vinter and Trollope (1995) [2]. The alignment can then transfer to using the first described method in which the fields are calculated directly from the field definition at each of the field points of one or both of the molecules being compared.

As an extension to any of the above methods, the torsional angles of one or both molecules can be allowed to change during the optimisation process. This allows the best possible fit between the two molecules to be found, even if the conformations used in the best overlay are not present in the starting set of conformations.

The similarity values obtained from aligning a series of molecules with a known active molecule can be used to predict the activities of those molecules by using the similarity values as variables in any form of quantitative structure-activity relationship (QSAR) analysis. QSAR analysis is a standard term describing the calculation or measurement of one or more properties of a set of molecules and then attempting to relate the biological activities of the molecules to their properties (e.g. by regression).

Typically, a single overlay score will be calculated for the electrostatic field types, i.e. the positive and negative fields. Other field types, for example for a surface interaction field, will generally have a separate overlay score calculated. If the field definition includes multiple field types as is often the case, a weighted summation is performed to obtain an overall score. The weighting will generally be to ensure that contributions from different field types are approximately the same or weighted according to the relative significance one wishes to ascribe each field type for the particular study being undertaken.

An example is now described, which shows how the new scoring method can be advantageous. The new scoring method gives more realistic answers in regions of the molecule in which the fields are changing rapidly. The prior art method implicitly assumes that all field points have equal 'width' and in some cases that leads to obviously incorrect answers.

For example, take the electrostatic points shown in FIG. 1 for formic acid. There are two negative points with energies −12.9 and −11.4 and one positive point with energy 4.0. The negative field points are given negative pseudocharges in the prior art scoring formula as shown in the figure.

Suppose we are overlaying a second molecule with this molecule, and a positive field point of energy 4.0 is placed directly over the positive field point in the formic acid molecule. Intuitively, we know that this should improve the overlay score, as we are aligning regions of the two molecules with similar characteristics. However, the contribution to the score according to the prior art method is:

$$\begin{aligned} E_{AB} &= -\sum_{i,j} \frac{q_{iA} q_{jB}}{k + d_{iA,jB}} \\ &= -\frac{4.0 \times 4.0}{1+0} - \frac{4.0 \times (-11.4)}{1+3.5} - \frac{4.0 \times (12.9)}{1+5.4} \\ &= -16.0 + 10.13 + 8.06 \end{aligned}$$

-continued $$= +2.19$$

i.e. the overlay score is worse than if that point did not exist. This is clearly wrong. By contrast, in the method of the invention, the score from the same interaction is $$E_{AB} = -\sum_i q_{iA} f_B (\underline{p}_{iA})$$
$$= -4.0 \times 4.0$$
$$= -16.0$$

i.e. placing the positive field point from molecule B over the positive field point from molecule A (formic acid) improves the overlay score, in agreement with intuition.

An enhancement to the scoring method is to apply a non-linear scaling to provide the desirable property that two field points of a given size S become equivalent to one field point of size 2S in their contribution to the score. The non-linear scaling we use with the scoring formulae of the invention involves taking the square root of the absolute field value while preserving the sign (i.e. 4 becomes 2, −4 becomes −2).

The advantage of non-linear scaling becomes apparent in overlays. Suppose we have two molecules: molecule A has one large field point of size 10, while molecule B has two well-separated field points of size 5 each. We would intuitively like the overlay score of A on itself and B on itself to be roughly the same, as the sum of the field point sizes of the two molecules is the same. Unscaled, the overlay score of A on itself is 100 (10×10), while the overlay score of B on itself is only 50 (2×5×5). With this scaling, the overlay score of A on itself is 10 (sqrt(10)×sqrt(10)), and the overlay score of B on itself is also 10 (2×sqrt(5)×sqrt(5)). More generally, the difference with and without scaling will be $q^2$ v. $2(\frac{1}{2}q)^2$ where q is the energy value.

Figure 2:
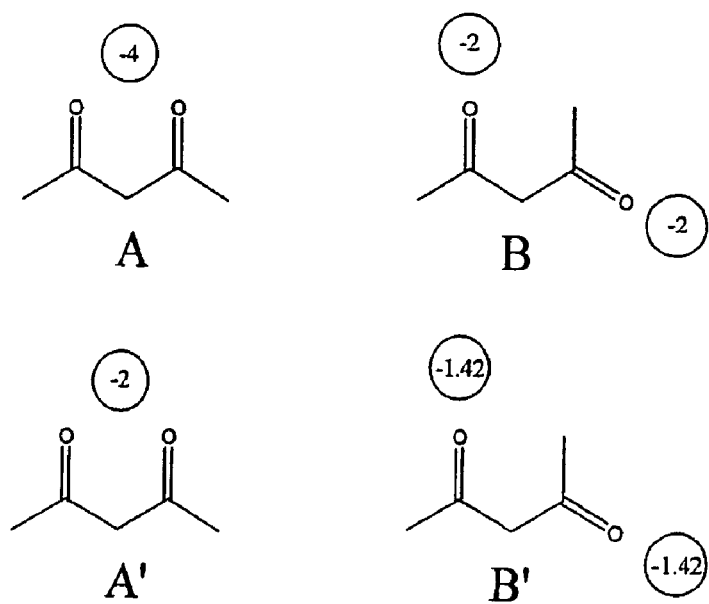
FIG. 2 shows the results of square root scaling of field point values which is used to transform molecule A into molecule A' and molecule B into molecule B'.

FIG. 2 illustrates another example using two molecules labelled A and B. Molecule A has one field point with a value of −4, while molecule B has two field points of value −2 each. Labels A' and B' represent molecules A and B after the scaling as described above.

It is noted that the non-linear square root scaling not only works with the overlay scoring method of the invention, but also with the prior art pseudo-Coulombic scoring method. By way of example, the following table shows the field overlay score of each molecule on itself using the prior art scoring pseudo-Coulombic formula given in the introduction with the parameters k=1, l=2.

| Field overlay | Score |
|---|---|
| A on A | 16.0 |
| B on B | 8.0 |
| A' on A' | 4.0 |
| B' on B' | 4.0 |

Square root scaling should work in this way for any overlay method which is based on taking the product of the energy values of field points of the two conformers. If scoring formulae are used which do not take the direct product of the energy values, it may well still be possible to provide a different non-linear scaling to provide the same desirable property that two field points of a given size become equivalent to one field point of twice the size in their contribution to the score.

It is noted that although this enhancement has been presented as being a scaling of the field point values, it could equally well be presented as a modification of the scoring formula. The presentational difference is of no substance.

REFERENCES

[1] J G Vinter: Journal of Computer-Aided molecular Design: volume 8 (1994) pages 653-668
[2] J G Vinter and K I Trollope: Journal of Computer-Aided molecular Design: volume 9 (1995) pages 297-307
[3] GB2317030A
[4] U.S. Pat. No. 5,703,792
[5] GB2266391A
[6] WO 98/47088A

The invention claimed is:

1. A computer-implemented method of identifying candidate molecules having a known biological activity or physicochemical property, the method comprising:
   providing a set of field points representing field extrema of a first molecule, wherein each field point has a position and a field size value, the molecule having a known biological activity or physicochemical property;
   using a processor to determine at the position of each of the field points of the first molecule the field of a second molecule to obtain a set of field sample values;
   combining the field sample values of the second molecule with the field size values of the first molecule to provide a score indicative of the field similarity of the first molecule to the second molecule, wherein the field is an electrostatic field; and
   providing a measure of the second molecule to have the known biological activity or physicochemical property based on the score.

2. The method of claim 1, wherein the field sample values are determined by applying the position of each of the field points to a field definition formula.

3. The method of claim 1, wherein the field sample values are determined by calculating the field by interpolation from a pre-calculated grid of field size values around the second molecule.

4. The method of claim 1, wherein, during the combining, the field size values are transformed to scaled field size values such that two field points having a first field size value give the same contribution to the score as one field point having a field size value twice the first field size value.

5. The method of claim 4, wherein the scaled field size values have the magnitude of the square root of the absolute value of the field size values and the sign of the field size values.

6. The method of claim 1, wherein combining the field sample values and the field size values involves obtaining their product.

7. The method of claim 1, further comprising:
   providing a second set of field points representing field extrema of the second molecule, wherein each field point has a position and a field size value;
   using a processor to determine at the position of each of the field points of the second set the field of the first molecule to obtain a further set of field sample values;
   combining the further field sample values with the field size values of the field points of the second set to obtain a further score, wherein the further score is indicative of the field similarity of the second molecule to the first molecule; and combining the further score with the score of the field similarity of the first molecule to the second molecule to provide an aggregate score.

8. The method of claim 7, wherein the further field sample values are determined by applying the position of each of the field points of the second set to a field definition formula.

9. The method of claim 7, wherein the further field sample values are determined by calculating the field by interpolation from a pre-calculated grid of field size values around the first molecule.

10. The method of claim 7, wherein combining the further field sample values and the field size values involves obtaining their product.

11. The method of claim 1, wherein the field size values are energy values.

12. The method of claim 1, wherein the field extrema are field minima.

13. A non-transitory computer interpretable recording medium bearing a set of instructions executable by a computer for carrying out the process of claim 1.

14. A computer apparatus comprising the computer interpretable recording medium of claim 13.

* * * * *